(12) United States Patent
Fan et al.

(10) Patent No.: US 11,938,629 B2
(45) Date of Patent: Mar. 26, 2024

(54) MICRO-ROBOT MAGNETIC DRIVE DEVICE AND CONTROL METHOD BASED ON DOUBLE CLOSED LOOP THREE-DIMENSIONAL PATH TRACKING

(71) Applicant: JIANGNAN UNIVERSITY, Wuxi (CN)

(72) Inventors: Qigao Fan, Wuxi (CN); Wei Chen, Wuxi (CN); Linbai Xie, Wuxi (CN); Yixin Zhu, Wuxi (CN); Guofeng Yang, Wuxi (CN); Yueyang Li, Wuxi (CN); Kaitao Bi, Wuxi (CN); Wentao Huang, Wuxi (CN); Haichi Luo, Wuxi (CN); Zhengqing Zhao, Wuxi (CN)

(73) Assignee: JIANGNAN UNIVERSITY, Jiangsu (CN)

(*) Notice: Subject to any disclaimer, the term of this patent is extended or adjusted under 35 U.S.C. 154(b) by 399 days.

(21) Appl. No.: 17/522,676

(22) Filed: Nov. 9, 2021

(65) Prior Publication Data

US 2022/0118609 A1  Apr. 21, 2022

Related U.S. Application Data

(63) Continuation of application No. PCT/CN2021/104466, filed on Jul. 5, 2021.

(30) Foreign Application Priority Data

Oct. 19, 2020  (CN) .......................... 202011118436.2

(51) Int. Cl.
*B25J 9/12* (2006.01)
*B25J 7/00* (2006.01)
*B25J 9/16* (2006.01)

(52) U.S. Cl.
CPC ................. *B25J 9/126* (2013.01); *B25J 7/00* (2013.01); *B25J 9/1602* (2013.01); *B25J 9/1664* (2013.01); *B25J 9/1697* (2013.01)

(58) Field of Classification Search
CPC .. B25J 9/126; B25J 7/00; B25J 9/1602; A61B 2034/2065
See application file for complete search history.

(56) References Cited

U.S. PATENT DOCUMENTS

| 5,720,010 A | 2/1998 | Watanabe et al. |
| 2014/0253114 A1 | 9/2014 | Khamesee et al. |

(Continued)

FOREIGN PATENT DOCUMENTS

| CN | 101262198 A | 9/2008 |
| CN | 105334964 A | 2/2016 |

(Continued)

OTHER PUBLICATIONS

Luo et al., A collaborative positioning algorithm for mobile target using multisensor data integration in enclosed environments, Computer Communications 44 (2014) 26-35 (Feb. 28, 2014).

(Continued)

*Primary Examiner* — Ian Jen
*Assistant Examiner* — Renee LaRose
(74) *Attorney, Agent, or Firm* — SZDC Law PC

(57) ABSTRACT

A micro-robot magnetic drive device and a control method based on double closed loop three-dimensional path tracking are disclosed. The method includes: inputting a desired tracking path, obtaining current pose information of a magnetic micro-robot through a camera, and then calculating a position of a center of mass, an actual axial direction, coordinates of a desired position point with the shortest distance from the center of mass on a desired tracking path, and a tangent direction of this point; calculating a horizontal (Continued)

distance, a vertical distance, a direction angle error, and a pitch angle error of the two points according to the actual axial direction, the tangent direction, and disturbance compensation; and obtaining a required rotating magnetic field according to a designed position closed loop controller.

10 Claims, 6 Drawing Sheets

(56) References Cited

U.S. PATENT DOCUMENTS

| | | |
|---|---|---|
| 2014/0333143 A1 | 11/2014 | Kim et al. |
| 2020/0030995 A1 | 1/2020 | Lu et al. |

FOREIGN PATENT DOCUMENTS

| | | |
|---|---|---|
| CN | 108199527 A | 6/2016 |
| CN | 107179780 A | 9/2017 |
| CN | 108406725 A | 8/2018 |
| CN | 112180736 A | 1/2021 |

OTHER PUBLICATIONS

Fan et al., Data Fusion for Indoor Mobile Robot Positioning Based on Tightly Coupled INS/UWB, The Journal of Navigation, vol. 70, Issue 5, Sep. 2017, pp. 1079-1097 (Apr. 17, 2017).

Zhu et al., Loss and temperature rise analysis of robot permanent magnet motor based on field-circuit coupling, Electrical Engineering, vol. 21, No. 6, pp. 7-12 (Jun. 30, 2020).

Song, Study on magnetic microrobot actuation method based on three-dimensional adjustable magnetic field, Harbin Institute of Technology Master's Thesis (Jan. 31, 2018).

(a)

(b)

(c)

MICRO-ROBOT MAGNETIC DRIVE DEVICE AND CONTROL METHOD BASED ON DOUBLE CLOSED LOOP THREE-DIMENSIONAL PATH TRACKING

This application is a Continuation Application of PCT/CN2021/104466, filed on Jul. 5, 2021, which claims priority to Chinese Patent Application No. 202011118436.2, filed on Oct. 19, 2020, which is incorporated by reference for all purposes as if fully set forth herein.

TECHNICAL FIELD

The present invention relates to the field of micro-nano robot control technologies, and in particular, to a micro-robot magnetic drive device and a control method based on double closed loop three-dimensional path tracking.

BACKGROUND

Miniaturized robots provide solutions for a variety of applications in complex and dangerous environments. Electromagnetically driven magnetic micro-robots are applicable to medical environments, and magnetic micro-robots can be used to carry and transport drugs to achieve minimally invasive treatment without harming the human body. In order to perform such tasks, magnetic micro-robots should be able to track a desired path. Path tracking control of existing magnetic micro-robots is mostly applied to a plane, and single closed loop path tracking is widely used. That is, pose information of a magnetic micro-robot in a plane is obtained through visual feedback of cameras, and a position closed loop is established to perform tracking in the plane. However, there are certain problems, including response delay and low adaptability. On one hand, due to response delay of a magnetic field generating device in a high frequency environment, an applied driving device often cannot establish a required magnetic field in time and accurately, resulting in a slow response speed. On the other hand, for a complex human environment, it is expected that a magnetic micro-robot can complete the tracking of a three-dimensional path. The above-mentioned method is feasible in the field of planar path tracking control. However, the above-mentioned control method is of no avail in applications to path tracking in a three-dimensional environment.

SUMMARY

In view of the above-mentioned problem and technical requirements, the inventor proposes a micro-robot magnetic drive device and a control method based on double closed loop three-dimensional path tracking to achieve accurate and timely tracking of a given three-dimensional desired tracking path, and overcome a problem of a slow response speed of a magnetic drive device under high-frequency conditions. Double closed loop control with position feedback and current feedback is used to improve the accuracy and rapidity of three-dimensional path tracking.

The technical solutions of the present invention are as follows.

A micro-robot magnetic drive device based on double closed loop three-dimensional path tracking includes an electromagnetic coil module, a direct current (DC) current source module, a pulse-width modulation (PWM) inverter circuit, a current sensor, a host computer, and two cameras, the electromagnetic coil module includes six first-level iron cores with trapezoidal probes, Helmholtz coils arranged on the first-level iron cores, and coil supports, each pair of first-level iron cores with trapezoidal probes and Helmholtz coils corresponding to the pair of first-level iron cores are arranged in parallel, the coil supports are configured to fix three pairs of first-level iron cores with trapezoidal probes and three pairs of Helmholtz coils, the three pairs of first-level iron cores with trapezoidal probes are orthogonal to each other in an axial direction, the three pairs of Helmholtz coils are orthogonal to each other in an axial direction, a region formed on an inner side of the three pairs of trapezoidal probes is used as a working space for a magnetic micro-robot, each DC current source passes through the PWM inverter circuit to provide an alternating current to one pair or one of the Helmholtz coils, the host computer is separately connected to the PWM inverter circuit, the current sensor, and the cameras, the current sensor is configured to detect an output current of the Helmholtz coil, the two cameras are arranged on an outer side of the coil supports and are orthogonally distributed, the host computer sends a control signal to the PWM inverter circuit to output an alternating current with adjustable frequency and amplitude, the Helmholtz coil generates a rotating magnetic field to control the magnetic micro-robot to perform three-dimensional movement in an axial direction of the rotating magnetic field, and the cameras obtain position information of the magnetic micro-robot and transmit the position information to the host computer to implement closed loop control of the three-dimensional movement of the magnetic micro-robot.

In a further technical solution of the present invention, the coil supports include bases arranged vertically opposite to each other, supports, and a hollow baffle, each base is provided with three triangular inclined blocks in an axial direction, inclined surfaces of a pair of triangular inclined blocks in an axial direction are arranged in parallel and are configured to place the first-level iron cores with trapezoidal probes, the supports are arranged between the bases for support, the hollow baffle is arranged in the middle of the supports and parallel to the bases, the hollow baffle divides a space defined by the bases into an upper region and a lower region, each pair of first-level iron cores with trapezoidal probes and one of the Helmholtz coils corresponding to the pair of first-level iron cores are arranged on the hollow baffle and are located in the upper region, the other of the Helmholtz coils is located in the lower region, and a hollow area of the hollow baffle is at least the same as an area of the working space of the magnetic micro-robot.

In a further technical solution of the present invention, the first-level iron cores are cylindrical iron cores made of DT4-E material with a diameter of 50 mm and a thickness of 30 mm, the number of turns of each Helmholtz coil is 190, a distal end of each trapezoidal probe is a square with a side length of 35 mm, a front end of the trapezoidal probe is a rectangle with a length of 16 mm and a width of 2 mm, the working space is a spherical space with a radius of 16 mm, and the magnetic micro-robot is in a helical shape.

A micro-robot control method based on double closed loop three-dimensional path tracking includes:
  inputting a desired tracking path into the host computer to obtain a desired direction of movement, where the cameras obtain current pose information of the magnetic micro-robot, and feed back the current pose information to the host computer to obtain three-dimensional coordinates of a center of mass and an actual axial direction of the magnetic micro-robot;

finding a desired position point with the shortest distance from the center of mass on the desired tracking path, and establishing a curve coordinate system of the desired tracking path to obtain three-dimensional coordinates of the desired position point and a curvature and a torsion of a curve of the desired tracking path;

processing the actual axial direction and the desired direction of movement to obtain a direction error and the three-dimensional coordinates of the center of mass and the three-dimensional coordinates of the desired position point to obtain a position error, where the direction error includes a pitch angle error and a direction angle error, and the position error includes a horizontal distance and a vertical distance between the center of mass and the desired position point;

modeling three-dimensional kinematics of the desired tracking path according to the curvature, the torsion, the direction error, and the position error to obtain state space equations;

designing a position closed loop controller through the state space equations to obtain a required rotating magnetic field, and inputting the rotating magnetic field into an established current closed loop magnetic field controller to output a desired magnetic field, to implement a double closed loop three-dimensional movement control of the magnetic micro-robot; and repeating the step of obtaining current pose information of the magnetic micro-robot, and feeding back the current pose information to the host computer to obtain three-dimensional coordinates of a center of mass and an actual axial direction of the magnetic micro-robot until the entire desired tracking path is tracked.

In a further technical solution of the present invention, the obtaining, by the cameras, current pose information of the magnetic micro-robot, and feeding back the current pose information to the host computer to obtain three-dimensional coordinates of a center of mass and an actual axial direction of the magnetic micro-robot includes:

detecting the current pose information of the magnetic micro-robot by using a side camera and a top camera, fixing a coordinate system of the top camera as a world coordinate system, and calculating an actual axial direction of the magnetic micro-robot in the world coordinate system by the following formula:
$X_B = {}^{ct}h_t \times {}^{ct}h_S = {}^{ct}h_t \times ({}^{ct}R_{cs}{}^{cs}h_s)$,
where ${}^{ct}h_t$ represents a normal vector of a plane of the top camera, ${}^{cs}h_s$ represents a normal vector of a plane of the side camera, ${}^{ct}h_s$ represents a transformation from the normal vector of the plane of the side camera to the plane of the top camera, ${}^{ct}R_{cs}$ represents a rotation matrix from a coordinate system of the side camera to the coordinate system of the top camera, and $X_B$ represents the actual axial direction of the magnetic micro-robot in the world coordinate system; and calculating three-dimensional coordinates of the center of mass of the magnetic micro-robot in the world coordinate system by the following formula:

$$G = {}^{ct}R_{cs}{}^{cs}G + {}^{ct}t_{cs},$$

where ${}^{cs}G$ represents coordinates of the center of mass in the plane of the side camera, ${}^{ct}t_{cs}$ represents a translation matrix from the coordinate system of the side camera to the coordinate system of the top camera, and G represents the three-dimensional coordinates of the center of mass in the world coordinate system.

In a further technical solution of the present invention, state space equations are:

$$\begin{cases} \dot{s} = \dfrac{v\cos\theta_{de}\cos\theta_{ie}}{1 - cd_y} \\ \dot{d}_y = v\sin\theta_{de}\cos\theta_{ie} + \tau d_z \dot{s} \\ \dot{d}_z = -v\sin\theta_{ie} - \tau d_y \dot{s} \\ \dot{\theta}_{ie} = \Omega_z \cos\delta_{\theta i} - \Omega_z \sin\delta_{\theta d}\sin\delta_{\theta i} - \delta_{\theta i}\cos\theta_{\theta d} + \tau \dot{s}\sin\theta_{de} \\ \dot{\theta}_{de} = \Omega_z \dfrac{\cos\delta_{\theta i}}{\cos\theta_{ie}} + \dfrac{\delta_{\theta d}}{\cos\theta_{ie}} - \tau \dot{s}\tan\theta_{ie}\cos\theta_{de} - c\dot{s} \end{cases},$$

where s represents the three-dimensional coordinates of the desired position point, v represents an actual movement speed, $v_{de}$ represents the direction angle error, $\theta_{ie}$ represents the pitch angle error, c represents the curvature, τ represents the torsion, $d_y$ represents the vertical distance, $d_z$ represents the horizontal distance, $\Omega_y$ represents an angular velocity component of the magnetic micro-robot on a Y axis, $\Omega_z$ represents an angular velocity component of the magnetic micro-robot on a Z axis, $\delta_{\theta i}$ represents a compensation pitch angle, and $\delta_{\theta d}$ represents a compensation direction angle.

In a further technical solution of the present invention, the designing a position closed loop controller through the state space equations to obtain a required rotating magnetic field includes:

linearizing the state space equations according to a chain rule and a path tracking task to obtain inputs of the position closed loop controller:

$$\begin{cases} u_1 = \dfrac{v\cos\theta_{de}\cos\theta_{ie}}{1 - cd_y} \\ u_2 = -k_{d1}u_1 d_y - k_{t1}|u_1|(\tau d_z + (1 - cd_y)\tan\theta_{de}) \\ u_3 = -k_{d2}u_1 d_y - k_{t2}|u_1|\left(-\tau d_y + (cd_y - 1)\cos\dfrac{1}{\theta_{de}}\tan\theta_{ie}\right) \end{cases},$$

where $k_{d1}$, $k_{t1}$, $k_{d2}$, and $k_{t2}$ are control gains and are positive;

the path tracking task is configured to enable the direction angle error, the pitch angle error, the vertical distance, and the horizontal distance to converge to zero; and an output of the position closed loop controller is:

$$\begin{cases} \Omega_z = (u_2 - \gamma_{22})\gamma_{21}^{-1} \\ \Omega_y = (u_3 - \gamma_{33} - \gamma_{32}\gamma_{21}^{-1}(u_2 - \gamma_{22})\gamma_{31}^{-1}) \end{cases},$$

where specific expressions of $\gamma_{21}$, $\gamma_{22}$, $\gamma_{31}$, $\gamma_{32}$, and $\gamma_{33}$ are:

$$\begin{cases} \gamma_{21} = v\dot{s}^{-1}\cos^{-1}\theta_{de}\cos\delta_{\theta i} \\ \gamma_{22} = v\dot{s}^{-1}\cos^{-1}\theta_{de}\cos\delta_{\theta i} - \dot{s}\left(2v\dot{s}^{-1}\tau\sin\theta_{ie} + \tau^2 d_y - d_z\frac{\partial\tau}{\partial s} + c(cd_y-1)(1-2\cos^{-2}\theta_{de}) + \left(c\tau d_z + d_y\frac{\partial c}{\partial s}\right)\tan\theta_{de}\right) \\ \gamma_{31} = v\dot{s}^{-1}\cos^{-1}\theta_{\theta i}\cos\delta_{ie} \\ \gamma_{32} = v\dot{s}^{-1}\cos^{-1}\theta_{ie}(\sin\delta_{\theta i}\sin\delta_{\theta d} - \cos\delta_{\theta i}\sin\theta_{ie}\tan\theta_{de}) \\ \gamma_{33} = \left(-d_y\frac{\partial\tau}{\partial s} - (d_z\tau + 2(1-cd_y)\tan\theta_{de})\left(\tau + c\frac{\tan\theta_{ie}}{\cos\theta_{de}}\right) + d_y\frac{\partial c}{\partial s}\frac{\tan\theta_{ie}}{\cos\theta_{de}}\right)\dot{s} + (1-cd_y)(\delta_{\theta i}\cos\delta_{\theta d} - \delta_{\theta d}\sin\theta_{ie}\tan\theta_{de}) \end{cases}$$

The required rotating magnetic field is calculated by the following formulas:

$$B_\perp = B_0\cos(2\pi ft)y_b + B_0\sin(2\pi ft)z_b,$$
$$B_\| = -\text{sgn}((B_\perp \times \Omega)X_b)\lambda\|(I_1 - X_B X_B^T)\Omega\|X_B,$$
$$B = B_\| + B_\perp,$$

where $V_\perp$ is a magnetic field perpendicular to an axial direction and is configured to provide rotation for the magnetic micro-robot, $B_\|$ is a magnetic field parallel to the axial direction and is configured to provide steering for the magnetic micro-robot, $B_0$ is a magnetic flux density of a center of a working space, f is a rotation frequency, t is a rotation time, $y_b$ and $z_b$ are basis vectors of a $X_B$ plane perpendicular to the actual axial direction of the magnetic micro-robot, $\lambda$ is a control gain, $\Omega$ is the output of the position closed loop controller, $\Omega=[\Omega_x, \Omega_y, \Omega_z]$, and $I_1$ represents a third order identity matrix.

In a further technical solution of the present invention, the inputting the rotating magnetic field into an established current closed loop magnetic field controller to output a desired magnetic field includes:

analyzing, by the current closed loop magnetic field controller, a direction of the rotating magnetic field and a coil output current fed back by the current sensor to output the control signal to the PWM inverter circuit, and outputting, by the PWM inverter circuit, a desired current to the Helmholtz coil to generate the desired magnetic field, $$B = \begin{bmatrix} B_X \\ B_Y \\ B_Z \end{bmatrix} = \frac{B_0\cos(2\pi ft)}{\sqrt{n^2_x + n^2_y}}\begin{bmatrix} n_y \\ -n_x \\ 0 \end{bmatrix} + \frac{B_0\sin(2\pi ft)}{\sqrt{(n_y n_z)^2 + (-n_y n_z)^2 + (-n^2_x - n^2_y)^2}}\begin{bmatrix} n_y n_z \\ -n_y n_z \\ -n^2_x - n^2_y \end{bmatrix},$$

where $B_X$, $B_Y$, and $B_Z$ are components of a magnetic field B in three axial directions, and $n_x$, $n_y$, and $n_z$ are unit direction quantities of three planes, including an XOY plane, an XOZ plane, and a YOZ plane; and decomposing a magnetic field into three axes, including an X axis, a Y axis, and a Z axis, a mapping relationship between a magnetic field and a current between the axes being as follows:

$$B = \left(\frac{4}{5}\right)^{\frac{3}{2}}\frac{\mu_0 NI}{a},$$

where $\mu_0$ is a magnetic field dielectric constant, N represents the number of turns of each Helmholtz coil, a represents a radius of the Helmholtz coil, and I represents the desired current flowing into the coil.

In a further technical solution of the present invention, in a case of no disturbance, a desired direction of movement of the magnetic micro-robot is an axial direction of the magnetic micro-robot, the desired direction of movement is represented by a first direction angle and a first pitch angle, the first direction angle is an angle between a projection of a vector $v_P$ to an XOY plane and an X axis, the first pitch angle is an angle between a vector $v_P$ and the XOY plane, due to the impact of gravity and disturbance, the actual axial direction of the magnetic micro-robot is represented by a second direction angle and a second pitch angle, and then a direction compensation is performed on the operating magnetic micro-robot to obtain a corresponding relationship between the actual axial direction and a desired direction of movement: $\theta_{d1}=\theta_d-\delta_{\theta d}$, and $\theta_{i1}=\theta_i-\delta_{\theta i}$, where $\theta_{d1}$ is the second direction angle, $\theta_d$ is the first direction angle, $\delta_{\theta d}$ is a compensation direction angle in a horizontal plane, the horizontal plane is the XOY plane, $\theta_{i1}$ is the second pitch angle, $\theta_i$ is the first pitch angle, $\delta_{\theta i}$ is a compensation pitch angle in a vertical plane, and the vertical plane is a plane perpendicular to the XOY plane;

the direction angle error is $\theta_{de}=\theta_{d1}-\theta_{dc}$, where $\theta_{dc}$ is a desired direction angle;

the pitch angle error is $\theta_{ie}=\theta_i-\delta_{\theta i}-\theta_{ic}$, where $\theta_{ic}$ is a desired pitch angle;

an actual movement speed of the operating magnetic micro-robot is:

$$v = \frac{1}{\cos\delta_{\theta i}\cos\delta_{\theta d}}v_P,$$

where $v_P$ is a desired movement speed, and v is an actual movement speed.

In a further technical solution of the present invention, the curve coordinate system of the desired tracking path is established with the desired position point as the origin, a tangential direction, a primary normal direction, and a secondary normal direction of the desired position point as coordinate axes, the tangential direction is the desired direction of movement, and a conversion relationship between the actual axial direction of the magnetic micro-robot and a first direction angle and a first pitch angle is obtained by the following formula:

$$X_B = \begin{bmatrix} \cos\theta_i \cos\theta_d \\ \cos\theta_i \sin\theta_d \\ \sin\theta_i \end{bmatrix}.$$

The present invention has the following beneficial effects.

A magnetic drive device provided in the present application can generate a rotating magnetic field, and implement control of a magnetic micro-robot in any direction in a three-dimensional space. Cameras cooperate with a position closed loop controller and a current closed loop magnetic field controller that are integrated in a host computer to monitor in real time and control movement of the magnetic micro-robot. The PWM inverter circuit can shorten establishment time of a desired magnetic field and make the desired magnetic field more stable. The host computer can quickly provide coordinates of a desired position point and running track information of the magnetic micro-robot. The current closed loop magnetic field controller, the PWM inverter circuit, the Helmholtz coil, and the current sensor form a first closed loop control. In the first closed loop control, the current closed loop magnetic field controller analyzes a direction of the rotating magnetic field and an output current fed back by the current sensor to output the control signal to the PWM inverter circuit, and the PWM inverter circuit outputs a desired current to the Helmholtz coil to generate a desired magnetic field. The position closed loop controller, the current closed loop magnetic field controller, the PWM inverter circuit, the Helmholtz coil, the magnetic micro-robot, and the cameras form a second closed loop control. In the second closed loop control, the position closed loop controller is designed according to an error between pose information fed back by the cameras and a desired movement path to obtain a required rotating magnetic field. Through a double closed loop control method, accurate and fast path tracking of the magnetic micro-robot in a three-dimensional environment is implemented.

DETAILED DESCRIPTION

Specific implementations of the present invention will be briefly described below with reference to the accompanying drawings.

Figure 1:
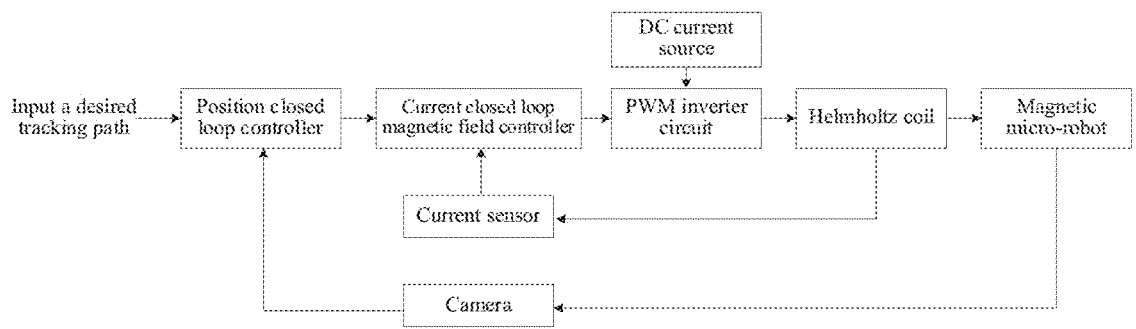
FIG. 1 is a schematic diagram of a magnetic drive device according to the present application.
Figure 2:
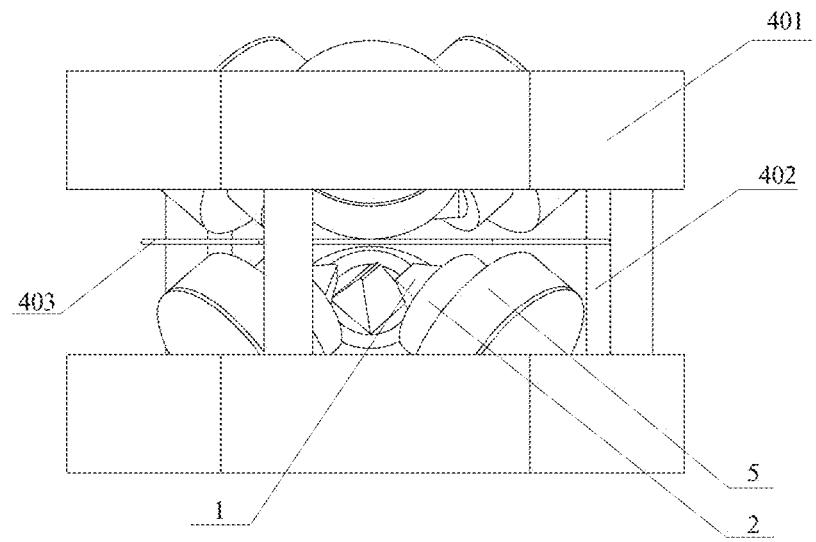
FIG. 2 is a front view of overall assembly of an electromagnetic coil module according to the present application.
Figure 3:
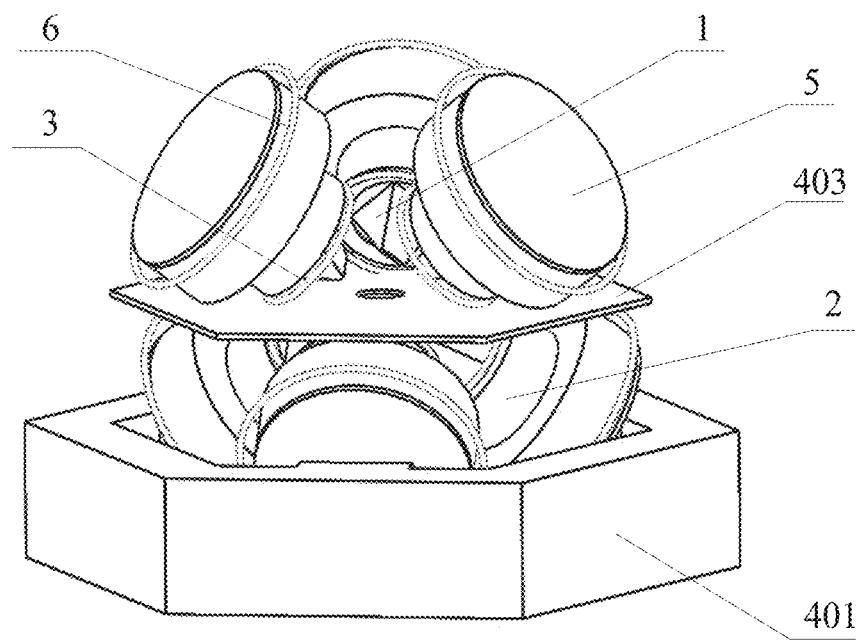
FIG. 3 is an assembly diagram of an electromagnetic coil module with a base and a support removed according to the present application.
Figure 4:
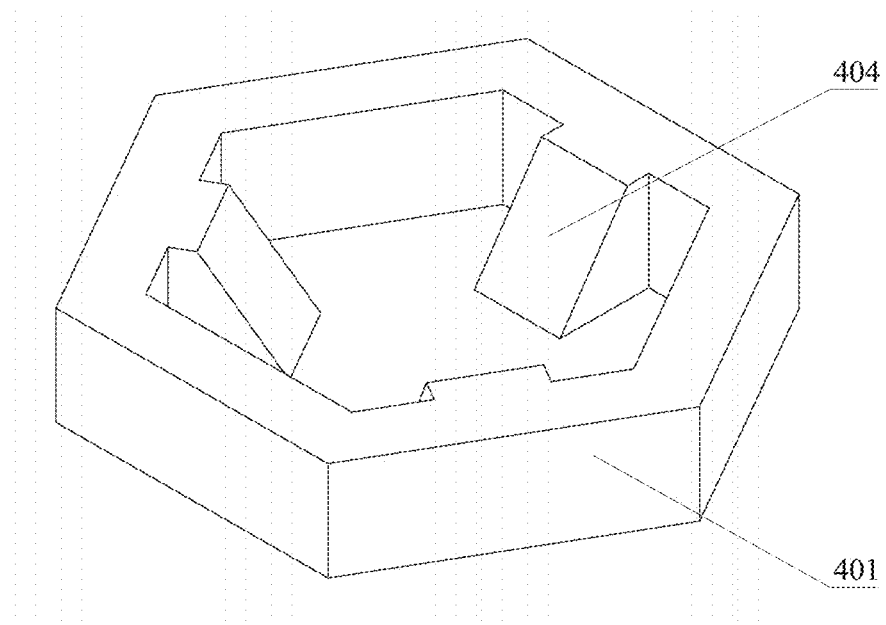
FIG. 4 is a schematic diagram of a base with a triangular inclined block according to the present application.

The present application discloses a micro-robot magnetic drive device based on double closed loop three-dimensional path tracking. FIG. 1 is a schematic diagram of a magnetic drive device. The magnetic drive device includes an electromagnetic coil module, a DC current source module, a PWM inverter circuit, a current sensor, a host computer, and two cameras. The PWM inverter circuit can shorten establishment time of a desired magnetic field and make the desired magnetic field more stable. The host computer can quickly provide coordinates of a desired position point and running track information of the magnetic micro-robot. As shown in FIG. 2 to FIG. 4, the electromagnetic coil module includes six first-level iron cores 2 with trapezoidal probes 1, Helmholtz coils 3 arranged on the first-level iron cores 2, and coil supports. Each pair of first-level iron cores 2 with trapezoidal probes 1 and the Helmholtz coils 3 corresponding to the pair of first-level iron cores are arranged in parallel. The coil supports are configured to fix three pairs of first-level iron cores 2 with trapezoidal probes 1 and three pairs of Helmholtz coils 3. Specifically, the coil supports include bases 401 arranged vertically opposite to each other, supports 402, and a hollow baffle 403. Each base 401 is provided with three triangular inclined blocks 404 in an axial direction. Inclined surfaces of a pair of triangular inclined blocks 404 in an axial direction are arranged in parallel and are configured to place the first-level iron cores 2 with trapezoidal probes 1. The supports 402 are arranged between the bases 401 for support. The hollow baffle 403 is arranged in the middle of the supports 402 and is parallel to the bases 401. The hollow baffle 403 divides a space defined by the bases 401 into an upper region and a lower region. Each pair of first-level iron cores 2 with trapezoidal probes 1 and one of the Helmholtz coils 3 corresponding to the pair of first-level iron cores are arranged on the hollow baffle 403 and are located in the upper region, and the other of the Helmholtz coils is located in the lower region.

The three pairs of first-level iron cores 2 with trapezoidal probes 1 are orthogonal to each other in an axial direction. The three pairs of Helmholtz coils 3 are orthogonal to each other in an axial direction. A region formed on an inner side of the three pairs of trapezoidal probes 1 is used as a working space of the magnetic micro-robot. A hollow area of the hollow baffle 403 is at least the same as an area of the working space of the magnetic micro-robot. Each DC current source passes through the PWM inverter circuit to provide an alternating current to one pair or one of the Helmholtz coils 3. That is, there are at least six DC current sources and at most twelve DC current sources in the present application. The host computer is separately connected to the PWM inverter circuit, the current sensor, and the cameras. The current sensor is configured to detect an output current of the Helmholtz coil 3. The two cameras are arranged on an outer side of the coil supports 402 and are orthogonally distributed. The host computer sends a control signal to the PWM inverter circuit to output an alternating current with adjustable frequency and amplitude. The Helmholtz coil 3 generates a rotating magnetic field to control the magnetic micro-robot to perform three-dimensional movement in an axial direction of the rotating magnetic field. The cameras obtain position information of the magnetic micro-robot and transmit the position information to the host computer to implement closed loop control of the three-dimensional movement of the magnetic micro-robot.

Optionally, the electromagnetic coil module further includes six secondary iron cores 5 and trapezoidal coils 6 arranged surrounding the six secondary iron cores. The secondary iron cores 5 are arranged on one side of the first-level iron core 2 without the trapezoidal probe 1. Similarly, each pair of secondary iron cores 5 are arranged in parallel and are placed on a triangular inclined block 404. Three pairs of secondary iron cores 5 are orthogonal to each other in an axial direction. The three pairs of trapezoidal coils 6 are orthogonal to each other in an axial direction. The trapezoidal probe 1, the first-level iron core 2, and the secondary iron core 5 are arranged in a step form.

Figure 5:
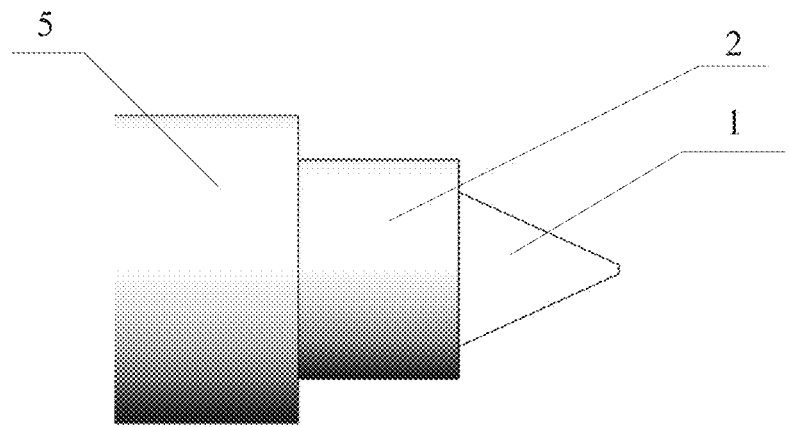
FIG. 5 is a three-view diagram of a combination of a trapezoidal probe, a first-level iron core, and a secondary iron core according to the present application.
Figure 5:
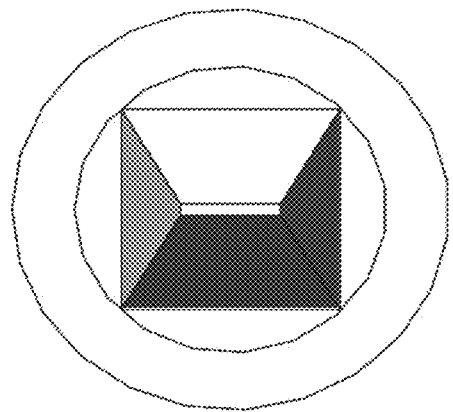
Figure 5:
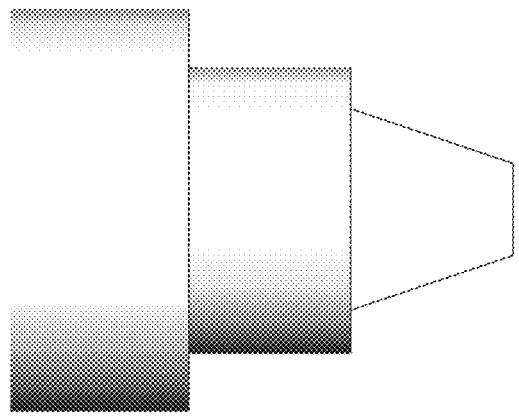

Optionally, FIG. 5(*a*) is a front view of a combination of a probe and an iron core. FIG. 5(*b*) is a side view of a combination of a probe and an iron core. FIG. 5(*c*) is a top view of a combination of a probe and an iron core. The first-level iron core 2 and the secondary iron core 5 are both cylindrical iron cores made of DT4-E material. The first-level iron core 2 has a diameter of 50 mm and a thickness of 30 mm. The number of turns of each Helmholtz coil 3 is 190. The secondary iron core 5 has a diameter of 70 mm and a thickness of 35 mm. The number of turns of each trapezoidal coil 6 is 610. The corresponding two coils are energized in series. A distal end of each trapezoidal probe 1 is a square with a side length of 35 mm, and a front end of the trapezoidal probe is a rectangle with a length of 16 mm and a width of 2 mm.

Optionally, the working space defined by the above-mentioned first-level iron cores 2 with trapezoidal probes 1 is a spherical space with a radius of 16 mm. The magnetic micro-robot is in a helical shape shown in FIG. 7.

Figure 6:
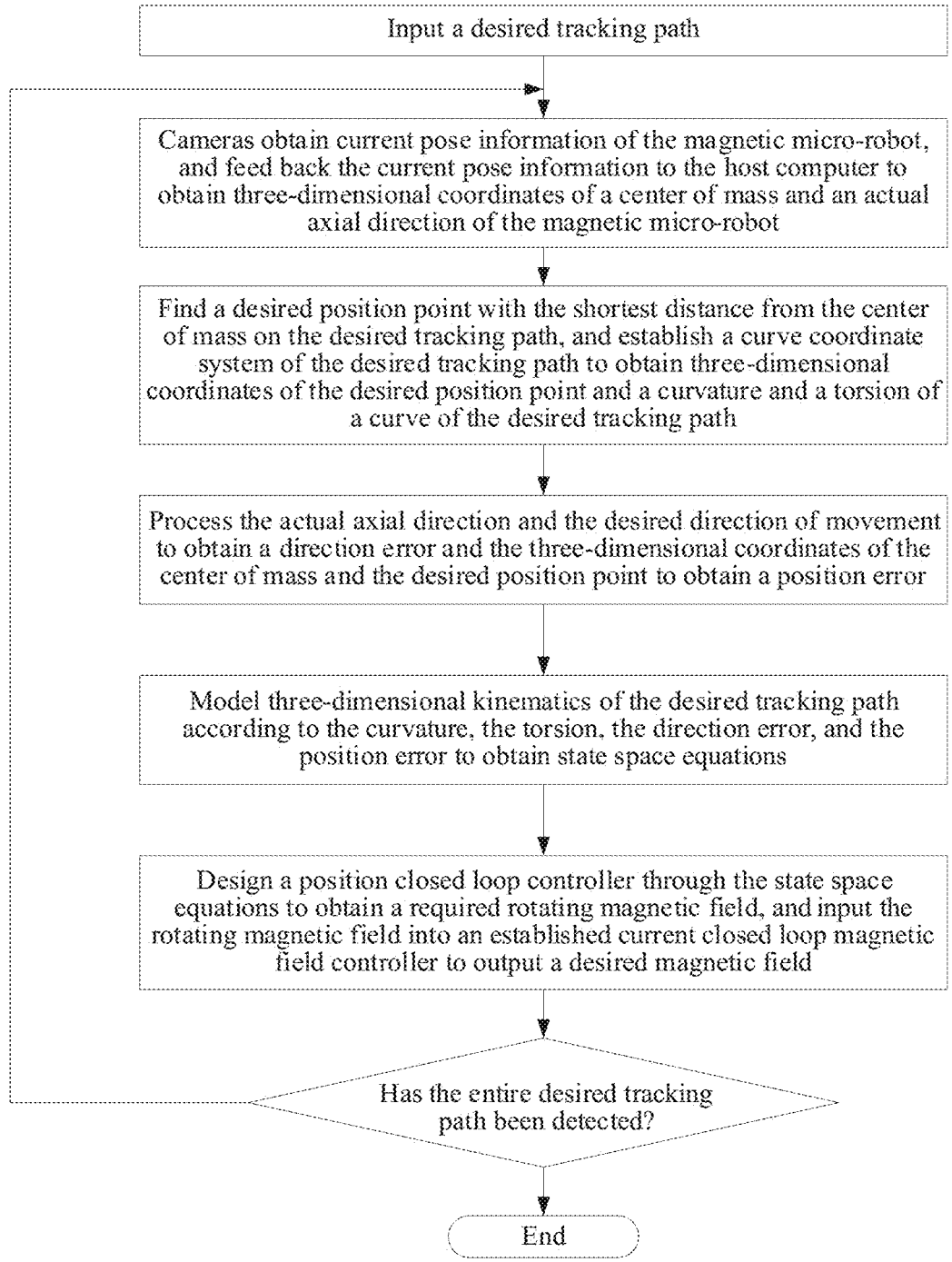
FIG. 6 is a flowchart of a control method according to the present application.

The present application further discloses a micro-robot control method based on double closed loop three-dimensional path tracking, which can be applied to the above-mentioned magnetic drive device. A flowchart of the control method is shown in FIG. 6 and includes the following steps.

Step 1: Input a desired tracking path into the host computer to obtain a desired direction of movement, where the cameras obtain current pose information of the magnetic micro-robot, and feed back the current pose information to the host computer to obtain three-dimensional coordinates of a center of mass and an actual axial direction of the magnetic micro-robot.

Figure 7:
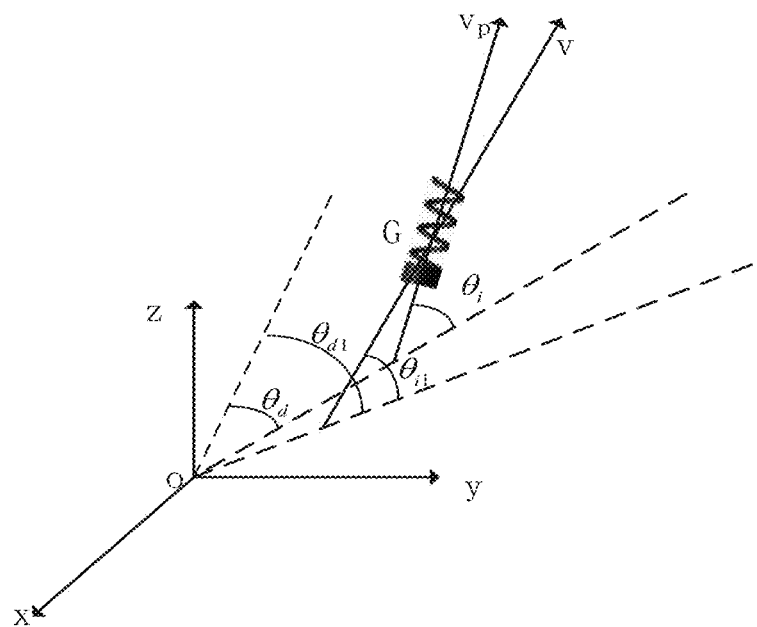
FIG. 7 is a schematic diagram of an angle compensation of a magnetic micro-robot moving in a three-dimensional space according to the present application.

As shown in FIG. 7, in a case of no disturbance, a desired direction of movement of the magnetic micro-robot is an axial direction of the magnetic micro-robot, the desired direction of movement is represented by a first direction angle and a first pitch angle, the first direction angle is an angle between a projection of a vector $v_P$ to an XOY plane and an X axis, and the first pitch angle is an angle between a vector $v_P$ and the XOY plane. Due to the impact of gravity and disturbance, the actual axial direction of the magnetic micro-robot is represented by a second direction angle and a second pitch angle, and then a direction compensation is performed on the operating magnetic micro-robot to obtain a corresponding relationship between the actual axial direction and a desired direction of movement: $\theta_{d1} = \theta_d - \delta_{\theta d}$, and $\theta_{i1} = \theta_i - \delta_{\theta i}$, where $\theta_{d1}$ the second direction angle, $\theta_d$ is the first direction angle, $\delta_{\theta d}$ is a compensation direction angle in a horizontal plane, the horizontal plane is the XOY plane, is the second pitch angle, $\theta_i$ is the first pitch angle, $\delta_{\theta i}$ is a compensation pitch angle in a vertical plane, and the vertical plane is a plane perpendicular to the XOY plane.

An actual movement speed of the operating magnetic micro-robot is:

$$v = \frac{1}{\cos\delta_{\theta i} \cos\delta_{\theta d}} v_P,$$

where $v_P$ is a desired movement speed, and v is an actual movement speed.

Figure 8:
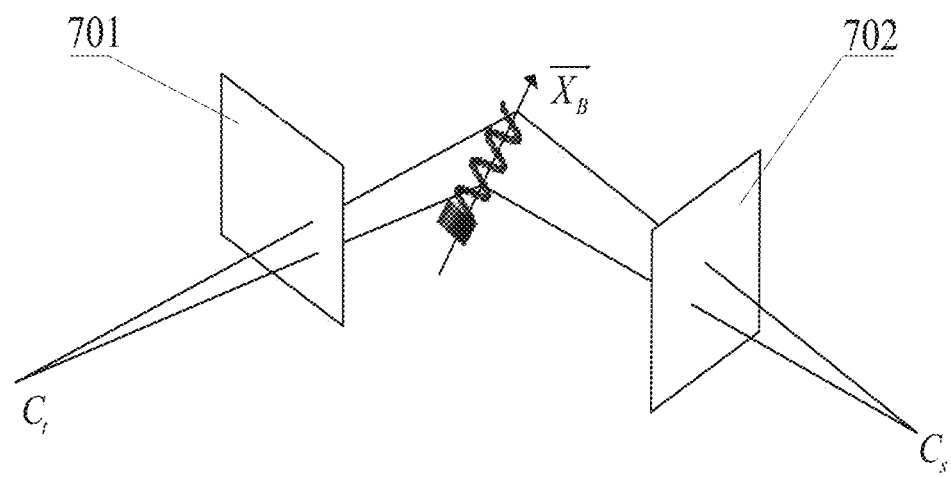
FIG. 8 is a schematic diagram of a principle of obtaining three-dimensional coordinates of a center of mass and an actual axial direction of a magnetic micro-robot according to the present application.

As shown in FIG. 8, the obtaining, by the cameras, current pose information of the magnetic micro-robot, and feeding back the current pose information to the host computer to obtain three-dimensional coordinates of a center of mass and an actual axial direction of the magnetic micro-robot includes:

detecting the current pose information of the magnetic micro-robot by using a side camera and a top camera, fixing a coordinate system of the top camera as a world coordinate system, and calculating an actual axial direction of the magnetic micro-robot in the world coordinate system by the following formula:
$X_B = {}^{ct}h_t \times {}^{ct}h_s = {}^{ct}h_t \times ({}^{ct}R_{cs}{}^{cs}h_s),$ where ${}^{ct}h_t$ represents a normal vector of a plane 701 of the top camera, ${}^{cs}h_s$ represents a normal vector of a plane 702 of the side camera, ${}^{ct}h_s$ represents a transformation from the normal vector of the plane 702 of the side camera to the plane 701 of the top camera, ${}^{ct}R_{cs}$ represents a rotation matrix from a coordinate system of the side camera to the coordinate system of the top camera, and $X_B$ represents the actual axial direction of the magnetic micro-robot in the world coordinate system; and calculating three-dimensional coordinates of the center of mass of the magnetic micro-robot in the world coordinate system by the following formula:

$$G = {}^{ct}R_{cs}{}^{cs}G + {}^{ct}t_{cs},$$

where ${}^{cs}G$ represents coordinates of the center of mass in the plane 702 of the side camera, ${}^{ct}t_{cs}$ represents a translation matrix from the coordinate system of the side camera to the coordinate system of the top camera, and G represents the three-dimensional coordinates of the center of mass in the world coordinate system.

Step 2: Find a desired position point with the shortest distance from the center of mass on the desired tracking path, and establish a curve coordinate system of the desired tracking path to obtain three-dimensional coordinates of the desired position point and a curvature and a torsion of a curve of the desired tracking path.

Figure 9:
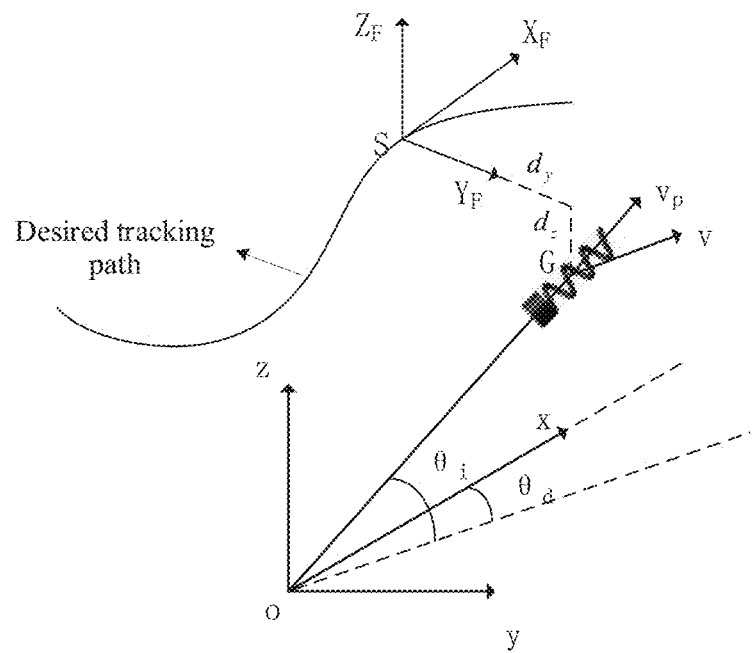
FIG. 9 is a model diagram of a desired tracking path of a magnetic micro-robot in a tracking path curve coordinate system according to the present application.

As shown in FIG. 9, the curve coordinate system of the desired tracking path is obtained by establishing an SF coordinate system with the desired position point s as the origin, a tangential direction $X_F$, a primary normal direction $Y_F$, and a secondary normal direction $Z_F$ of the desired position point as coordinate axes. The tangential direction $X_F$ is the desired direction of movement. A conversion relationship between the actual axial direction of the magnetic micro-robot and a first direction angle and a first pitch angle is obtained by the following formula:

$$X_B = \begin{bmatrix} \cos\theta_i\cos\theta_d \\ \cos\theta_i\sin\theta_d \\ \sin\theta_i \end{bmatrix}.$$

Step 3: Process the actual axial direction and the desired direction of movement to obtain a direction error and the three-dimensional coordinates of the center of mass and the three-dimensional coordinates of the desired position point to obtain a position error, where the direction error includes a pitch angle error and a direction angle error, and the position error includes a horizontal distance and a vertical distance between the center of mass and the desired position point.

The direction angle error is $\theta_{de}=\theta_{d1}-\theta_{dc}$, where $\theta_{dc}$ is a desired direction angle.

The pitch angle error is $\theta_{ie}=\theta_i-\delta_{\theta i}-\theta_{ic}$, where $\theta_{ic}$ is a desired pitch angle.

A horizontal distance $d_z$ and a vertical distance $d_y$ are a Euclidean distance between the three-dimensional coordinates of the desired position point and the three-dimensional coordinates of the center of mass.

Step 4: Model three-dimensional kinematics of the desired tracking path according to the curvature, the torsion, the direction error, and the position error to obtain state space equations.

The state space equations are:

$$\begin{cases} \dot{s} = \dfrac{v\cos\theta_{de}\cos\theta_{ie}}{1-cd_y} \\ \dot{d}_y = v\sin\theta_{de}\cos\theta_{ie} + \tau d_z\dot{s} \\ \dot{d}_z = -v\sin\theta_{ie} - \tau d_y\dot{s} \\ \dot{\theta}_{ie} = \Omega_y\cos\delta_d - \Omega_z\sin\delta_d\sin\delta_{\theta i} - \dot{\delta}_{\theta i}\cos\delta_{\theta d} + \tau\dot{s}\sin\theta_{de} \\ \dot{\theta}_{de} = \Omega_z\dfrac{\cos\delta_i}{\cos\theta_{ie}} + \dfrac{\dot{\delta}_{\theta d}}{\cos\theta_{ie}} - \tau\dot{s}\tan\theta_{ie}\cos\theta_{de} - c\dot{s} \end{cases},$$

where s represents the three-dimensional coordinates of the desired position point, v represents an actual movement speed, $\theta_{de}$ represents the direction angle error, $\theta_{ie}$ represents the pitch angle error, c represents the curvature, r represents the torsion, $d_y$ represents the vertical distance, $d_z$ represents the horizontal distance, $\Omega_y$ represents an angular velocity component of the magnetic micro-robot on a Y axis, $\Omega_z$ represents an angular velocity component of the magnetic micro-robot on a Z axis, $\delta_{\theta i}$ represents a compensation pitch angle, and $\delta_{\theta d}$ represents a compensation direction angle.

Step 5: Design a position closed loop controller through the state space equations to obtain a required rotating magnetic field, and input the rotating magnetic field into an established current closed loop magnetic field controller to output a desired magnetic field, to implement a double closed loop three-dimensional movement control of the magnetic micro-robot.

The state space equations are linearized according to a chain rule and a path tracking task to obtain inputs of the position closed loop controller:

$$\begin{cases} u_1 = \dfrac{v\cos\theta_{de}\cos\theta_{ie}}{1-cd_y} \\ u_2 = -k_{d1}u_1d_y - k_{t1}|u_1|(\tau d_z + (1-cd_y)\tan\theta_{de}) \\ u_3 = -k_{d2}u_1d_z - k_{t2}|u_1|\left(-\tau d_y + (cd_y-1)\cos\dfrac{1}{\theta_{de}}\tan\theta_{ie}\right) \end{cases},$$

where $k_{d1}$, $k_{t1}$, $k_{d2}$, and $k_{t2}$ are control gains and are positive.

The path tracking task is configured to enable the direction angle error, the pitch angle error, the vertical distance, and the horizontal distance to converge to zero.

An output of the position closed loop controller is:

$$\begin{cases} \Omega_z = (u_2 - \gamma_{22})\gamma_{21}^{-1} \\ \Omega_y = (u_3 - \gamma_{33} - \gamma_{32}\gamma_{21}^{-1}(u_2 - \gamma_{22})\gamma_{31}^{-1}) \end{cases},$$

where specific expressions of $\gamma_{21}$, $\gamma_{22}$, $\gamma_{31}$, $\gamma_{32}$, and $\gamma_{33}$ are:

$$\begin{cases} \gamma_{21} = v\dot{s}^{-1}\cos^{-1}\theta_{de}\cos\delta_{\theta i} \\ \gamma_{22} = v\dot{s}^{-1}\cos^{-1}\theta_{de}\cos\delta_{\theta i} - \dot{s}\left(2v\dot{s}^{-1}\tau\sin\theta_{ie} + \tau^2 d_y - d_z\dfrac{\partial\tau}{\partial s} + c(cd_y-1)(1-2\cos^{-2}\theta_{de}) + \left(c\tau d_z + d_y\dfrac{\partial c}{\partial s}\right)\tan\theta_{de}\right) \\ \gamma_{31} = v\dot{s}^{-1}\cos\delta_{\theta i}\cos^{-1}\theta_{ie} \\ \gamma_{32} = v\dot{s}^{-1}\cos^{-1}\theta_{ie}(\sin\delta_{\theta i}\sin\delta_{\theta d} - \cos\delta_{\theta i}\sin\theta_{ie}\tan\theta_{de}) \\ \gamma_{33} = \left(-d_y\dfrac{\partial\tau}{\partial s} - (d_z\tau + 2(1-cd_y)\tan\theta_{de})\left(\tau + c\dfrac{\tan\theta_{ie}}{\cos\theta_{de}}\right) + d_y\dfrac{\partial c}{\partial s}\dfrac{\tan\theta_{ie}}{\cos\theta_{de}}\right)\dot{s} + (1-cd_y)\left(\dot{\delta}_{\theta i}\cos\delta_{\theta d} - \dot{\delta}_{\theta d}\sin\theta_{ie}\tan\theta_{de}\right) \end{cases}.$$

The required rotating magnetic field is calculated by the following formulas:

$$B_\perp = B_0\cos(2\pi ft)y_b + B_0\sin(2\pi ft)z_b,$$

$$B_\| = -sgn((B_\perp \times \Omega)X_B)\lambda\|(I_1 - X_B X_B^T)\Omega\|X_B,$$

$$B = B_\| + B_\perp,$$

where $B_\perp$ is a magnetic field perpendicular to an axial direction and is configured to provide rotation for the magnetic micro-robot, $B_\|$ is a magnetic field parallel to the axial direction and is configured to provide steering for the magnetic micro-robot, $B_0$ is a magnetic flux density of a center of a working space, f is a rotation frequency, t is a rotation time, $y_b$ and $z_b$ are basis vectors of a $X_B$ plane perpendicular to the actual axial direction of the magnetic micro-robot, a is a control gain, $\Omega$ is the output of the position closed loop controller, $\Omega=[\Omega_x, \Omega_y, \Omega_z]$, and $I_1$ represents a third order identity matrix.

Figure 10:
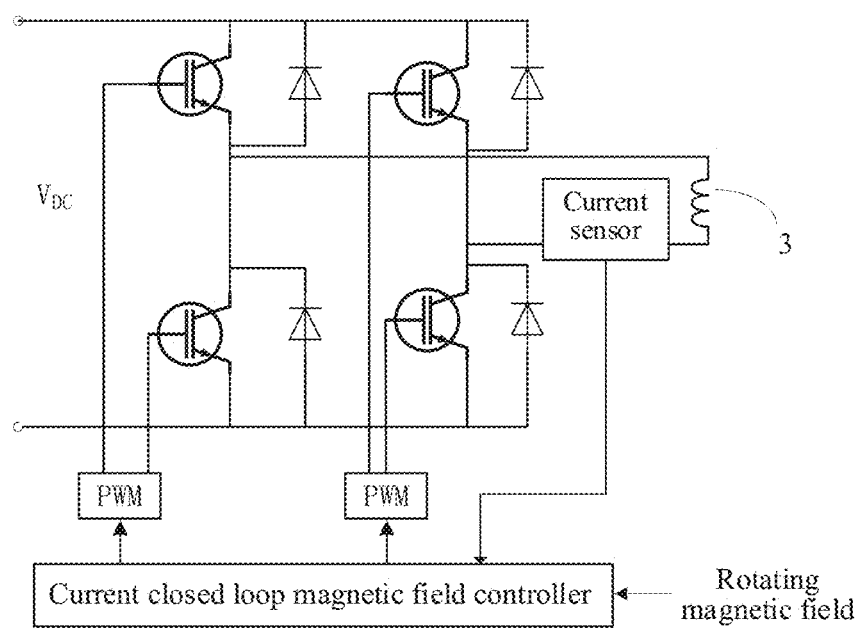
FIG. 10 is a partial circuit diagram of a first closed loop control according to the present application.

FIG. 10 is a partial circuit diagram of a first closed loop control. The current closed loop magnetic field controller analyzes a direction of the rotating magnetic field and a coil output current fed back by the current sensor to output a PWM control signal to the PWM inverter circuit. The PWM inverter circuit outputs a desired current to the Helmholtz coil 3 to generate the desired magnetic field.

$$B = \begin{bmatrix} B_X \\ B_Y \\ B_Z \end{bmatrix} =$$

$$\frac{B_0 \cos(2\pi ft)}{\sqrt{n_x^2 + n_y^2}} \begin{bmatrix} n_y \\ -n_x \\ 0 \end{bmatrix} + \frac{B_0 \sin(2\pi ft)}{\sqrt{(n_y n_z)^2 + (-n_y n_z)^2 + (-n_x^2 - n_y^2)^2}} \begin{bmatrix} n_y n_z \\ -n_y n_z \\ -n_x^2 - n_y^2 \end{bmatrix},$$

$B_X$, $B_Y$, and $B_Z$ are components of a magnetic field B in three axial directions, and $n_x$, $n_y$ and $n_z$ are unit direction quantities of three planes, including an XOY plane, an XOZ plane, and a YOZ plane.

A magnetic field are decomposed into three axes, including an X axis, a Y axis, and a Z axis, a mapping relationship between a magnetic field and a current between the axes being as follows:

$$B = \left(\frac{4}{5}\right)^{\frac{3}{2}} \frac{\mu_0 NI}{a},$$

where $\mu_0$ is a magnetic field dielectric constant, N represents the number of turns of each Helmholtz coil 3, a represents a radius of the Helmholtz coil 3, and I represents the desired current flowing into the coil.

Step 6: Repeat the step of obtaining current pose information of the magnetic micro-robot, and feeding back the current pose information to the host computer to obtain three-dimensional coordinates of a center of mass and an actual axial direction of the magnetic micro-robot until the entire desired tracking path is tracked.

In the present application, the current closed loop magnetic field controller and the position closed loop controller are designed in the host computer. The current closed loop magnetic field controller, the PWM inverter circuit, the Helmholtz coil, and the current sensor form a first closed loop control. In the first closed loop control, the current closed loop magnetic field controller outputs a control signal to the PWM inverter circuit, and the PWM inverter circuit outputs a desired current to the Helmholtz coil to generate a desired magnetic field. The position closed loop controller, the current closed loop magnetic field controller, the PWM inverter circuit, the Helmholtz coil, the magnetic micro-robot, and the cameras form a second closed loop control. In the second closed loop control, the position closed loop controller is designed according to an error between pose information fed back by the cameras and a desired movement path to obtain a required rotating magnetic field. Through a double closed loop control method, accurate and fast path tracking of the magnetic micro-robot in a three-dimensional environment is implemented.

The above descriptions are merely preferred implementations of the present application, and the present invention is not limited to the above embodiments. It can be understood that other improvements and changes directly derived or associated by those skilled in the art, without departing from the spirit and conception of the present invention, shall all fall within the protection scope of the present invention.

What is claimed is:

1. A micro-robot magnetic drive device based on double closed loop three-dimensional path tracking, wherein the magnetic drive device comprises an electromagnetic coil module, a direct current (DC) current source module, a pulse-width modulation (PWM) inverter circuit, a current sensor, a host computer, and two cameras, the electromagnetic coil module comprises six first-level iron cores with trapezoidal probes, Helmholtz coils arranged on the first-level iron cores, and coil supports, each pair of first-level iron cores with trapezoidal probes and Helmholtz coils corresponding to the pair of first-level iron cores are arranged in parallel, the coil supports are configured to fix three pairs of first-level iron cores with trapezoidal probes and three pairs of Helmholtz coils, the three pairs of first-level iron cores with trapezoidal probes are orthogonal to each other in an axial direction, the three pairs of Helmholtz coils are orthogonal to each other in an axial direction, a region formed on an inner side of the three pairs of trapezoidal probes is used as a working space for a magnetic micro-robot, each DC current source passes through the PWM inverter circuit to provide an alternating current to one pair or one of the Helmholtz coils, the host computer is separately connected to the PWM inverter circuit, the current sensor, and the cameras, the current sensor is configured to detect an output current of the Helmholtz coil, the two cameras are arranged on an outer side of the coil supports and are orthogonally distributed, the host computer sends a control signal to the PWM inverter circuit to output an alternating current with adjustable frequency and amplitude, the Helmholtz coil generates a rotating magnetic field to control the magnetic micro-robot to perform three-dimensional movement in an axial direction of the rotating magnetic field, and the cameras obtain position information of the magnetic micro-robot and transmit the position information to the host computer to implement closed loop control of the three-dimensional movement of the magnetic micro-robot.

2. The micro-robot magnetic drive device based on double closed loop three-dimensional path tracking according to claim 1, wherein the coil supports comprise bases arranged vertically opposite to each other, supports, and a hollow baffle, each base is provided with three triangular inclined blocks in an axial direction, inclined surfaces of a pair of triangular inclined blocks in an axial direction are arranged in parallel and are configured to place the first-level iron cores with trapezoidal probes, the supports are arranged between the bases for support, the hollow baffle is arranged in the middle of the supports and is parallel to the bases, the hollow baffle divides a space defined by the bases into an upper region and a lower region, each pair of first-level iron cores with trapezoidal probes and one of the Helmholtz coils corresponding to the pair of first-level iron cores are arranged on the hollow baffle and are located in the upper region, the other of the Helmholtz coils is located in the lower region, and a hollow area of the hollow baffle is at least the same as an area of the working space of the magnetic micro-robot.

3. The micro-robot magnetic drive device based on double closed loop three-dimensional path tracking according to claim 1, wherein the first-level iron cores are cylindrical iron cores made of DT4-E material with a diameter of 50 mm and a thickness of 30 mm, the number of turns of each Helmholtz coil is 190, a distal end of each trapezoidal probe is a square with a side length of 35 mm, a front end of the trapezoidal probe is a rectangle with a length of 16 mm and a width of 2 mm, the working space is a spherical space with a radius of 16 mm, and the magnetic micro-robot is in a helical shape.

4. A micro-robot control method based on double closed loop three-dimensional path tracking, applied to the magnetic drive device according to claim 1, the control method comprising:

inputting a desired tracking path into the host computer to obtain a desired direction of movement, wherein the cameras obtain current pose information of the magnetic micro-robot, and feed back the current pose information to the host computer to obtain three-dimensional coordinates of a center of mass and an actual axial direction of the magnetic micro-robot;

finding a desired position point with the shortest distance from the center of mass on the desired tracking path, and establishing a curve coordinate system of the desired tracking path to obtain three-dimensional coordinates of the desired position point and a curvature and a torsion of a curve of the desired tracking path;

processing the actual axial direction and the desired direction of movement to obtain a direction error and the three-dimensional coordinates of the center of mass and the three-dimensional coordinates of the desired position point to obtain a position error, wherein the direction error comprises a pitch angle error and a direction angle error, and the position error comprises a horizontal distance and a vertical distance between the center of mass and the desired position point;

modeling three-dimensional kinematics of the desired tracking path according to the curvature, the torsion, the direction error, and the position error to obtain state space equations;

designing a position closed loop controller through the state space equations to obtain a required rotating magnetic field, and inputting the rotating magnetic field into an established current closed loop magnetic field controller to output a desired magnetic field, to implement a double closed loop three-dimensional movement control of the magnetic micro-robot; and repeating the step of obtaining current pose information of the magnetic micro-robot, and feeding back the current pose information to the host computer to obtain three-dimensional coordinates of a center of mass and an actual axial direction of the magnetic micro-robot until the entire desired tracking path is tracked.

5. The micro-robot control method based on double closed loop three-dimensional path tracking according to claim 4, wherein the obtaining, by the cameras, current pose information of the magnetic micro-robot, and feeding back the current pose information to the host computer to obtain three-dimensional coordinates of a center of mass and an actual axial direction of the magnetic micro-robot comprises:

detecting the current pose information of the magnetic micro-robot by using a side camera and a top camera, fixing a coordinate system of the top camera as a world coordinate system, and calculating an actual axial direction of the magnetic micro-robot in the world coordinate system by the following formula:
$X_B = {}^{ct}h_t \times {}^{ct}h_s = {}^{ct}h_t \times ({}^{ct}R_{cs}{}^{cs}h_s)$, wherein ${}^{ct}h_t$ represents a normal vector of a plane of the top camera, ${}^{cs}h_s$ represents a normal vector of a plane of the side camera, ${}^{ct}h_s$ represents a transformation from the normal vector of the plane of the side camera to the plane of the top camera, ${}^{ct}R_{cs}$ represents a rotation matrix from a coordinate system of the side camera to the coordinate system of the top camera, and $X_B$ represents the actual axial direction of the magnetic micro-robot in the world coordinate system; and calculating three-dimensional coordinates of the center of mass of the magnetic micro-robot in the world coordinate system by the following formula:

$$G = {}^{ct}R_{cs}{}^{cs}G + {}^{ct}t_{cs},$$

wherein ${}^{cs}G$ represents coordinates of the center of mass in the plane of the side camera, ${}^{ct}t_{cs}$ represents a translation matrix from the coordinate system of the side camera to the coordinate system of the top camera, and G represents the three-dimensional coordinates of the center of mass in the world coordinate system.

6. The micro-robot control method based on double closed loop three-dimensional path tracking according to claim 4, wherein the state space equations are:

$$\begin{cases} \dot{s} = \dfrac{v\cos\theta_{de}\cos\theta_{ie}}{1-cd_y} \\ \dot{d}_y = v\sin\theta_{de}\cos\theta_{ie} + \tau d_z \dot{s} \\ \dot{d}_z = -v\sin\theta_{ie} - \tau d_y \dot{s} \\ \dot{\theta}_{ie} = \Omega_y\cos\delta_{\theta d} - \Omega_z\sin\delta_{\theta d}\sin\delta_{\theta i} - \dot{\delta}_{\theta i}\cos\delta_{\theta d} + \tau \dot{s}\sin\theta_{de} \\ \dot{\theta}_{de} = \Omega_z\dfrac{\cos\delta_{\theta i}}{\cos\theta_{ie}} + \dfrac{\dot{\delta}_{\theta d}}{\cos\theta_{ie}} - \tau \dot{s}\tan\theta_{ie}\cos\theta_{de} - c\dot{s} \end{cases},$$

wherein s represents the three-dimensional coordinates of the desired position point, v represents an actual movement speed, $\theta_{de}$ represents the direction angle error, $\theta_{ie}$ represents the pitch angle error, c represents the curvature, τ represents the torsion, $d_y$ represents the vertical distance, $d_z$ represents the horizontal distance, $\Omega_y$ represents an angular velocity component of the magnetic micro-robot on a Y axis, $\Omega_z$ represents an angular velocity component of the magnetic micro-robot on a Z axis, $\delta_{\theta i}$ represents a compensation pitch angle, and $\delta_{\theta d}$ represents a compensation direction angle.

7. The micro-robot control method based on double closed loop three-dimensional path tracking according to claim 6, wherein the designing a position closed loop controller through the state space equations to obtain a required rotating magnetic field comprises:

linearizing the state space equations according to a chain rule and a path tracking task to obtain inputs of the position closed loop controller:

$$\begin{cases} u_1 = \dfrac{v\cos\theta_{de}\cos\theta_{ie}}{1-cd_y} \\ u_2 = -k_{d1}u_1 d_y - k_{t1}|u_1|(\tau d_z + (1-cd_y)\tan\theta_{de}) \\ u_3 = -k_{d2}u_1 d_z - k_{t2}|u_1|\left(-\tau d_y + (cd_y - 1)\cos\dfrac{1}{\theta_{de}}\tan\theta_{ie}\right) \end{cases},$$

wherein $k_{d1}$, $k_{t1}$, $k_{d2}$, and $k_{t2}$ are control gains and are positive;

the path tracking task is configured to enable the direction angle error, the pitch angle error, the vertical distance, and the horizontal distance to converge to zero; and an output of the position closed loop controller is:

$$\begin{cases} \Omega_z = (u_2 - \gamma_{22})\gamma_{21}^{-1} \\ \Omega_y = (u_3 - \gamma_{33} - \gamma_{32}\gamma_{21}^{-1}(u_2 - \gamma_{22})\gamma_{31}^{-1}) \end{cases},$$

wherein specific expressions of $\gamma_{21}$, $\gamma_{22}$, $\gamma_{31}$, $\gamma_{32}$, and $\gamma_{33}$ are:

$$\begin{cases} \gamma_{21} = v\dot{s}^{-1}\cos^{-1}\theta_{de}\cos\delta_{\theta i} \\ \gamma_{22} = v\dot{s}^{-1}\cos^{-1}\theta_{de}\cos\delta_{\theta i} - \dot{s}\left(2v\dot{s}^{-1}\tau\sin\theta_{ie} + \tau^2 d_y - d_z\frac{\partial\tau}{\partial s} + c(cd_y-1)(1-2\cos^{-2}\theta_{de}) + \left(c\tau d_z + d_y\frac{\partial c}{\partial s}\right)\tan\theta_{de}\right) \\ \gamma_{31} = v\dot{s}^{-1}\cos\delta_{\theta i}\cos^{-1}\theta_{ie} \\ \gamma_{32} = v\dot{s}^{-1}\cos^{-1}\theta_{ie}(\sin\delta_{\theta i}\sin\delta_{\theta d} - \cos\delta_{\theta i}\sin\theta_{ie}\tan\theta_{de}) \\ \gamma_{33} = \left(-d_y\frac{\partial\tau}{\partial s} - (d_z\tau + 2(1-cd_y)\tan\theta_{de})\left(\tau + c\frac{\tan\theta_{ie}}{\cos\theta_{de}}\right) + d_y\frac{\partial c}{\partial s}\frac{\tan\theta_{ie}}{\cos\theta_{de}}\right)\dot{s} + (1-cd_y)\left(\dot{\delta}_{\theta i}\cos\delta_{\theta d} - \dot{\delta}_{\theta d}\sin\theta_{ie}\tan\theta_{de}\right) \end{cases}$$

the required rotating magnetic field is calculated by the following formulas:

$$B_\perp = B_0\cos(2\pi ft)y_b + B_0\sin(2\pi ft)z_b,$$
$$B_\| = -\text{sgn}((B_\perp \times \Omega)X_b)\lambda\|(I_1 - X_B X_B^T)\Omega\|X_B,$$
$$B = B_\| + B_\perp,$$

wherein $B_\perp$ is a magnetic field perpendicular to an axial direction and is configured to provide rotation for the magnetic micro-robot, $B_\|$ is a magnetic field parallel to the axial direction and is configured to provide steering for the magnetic micro-robot, $B_0$ is a magnetic flux density of a center of a working space, f is a rotation frequency, t is a rotation time, $y_b$ and $z_b$ are basis vectors of a $X_B$ plane perpendicular to the actual axial direction of the magnetic micro-robot, $\lambda$ is a control gain, $\Omega$ is the output of the position closed loop controller, $\Omega=[\Omega_x\ \Omega_y\ \Omega_z]$, and $I_1$ represents a third order identity matrix.

8. The micro-robot control method based on double closed loop three-dimensional path tracking according to claim 7, wherein the inputting the rotating magnetic field into an established current closed loop magnetic field controller to output a desired magnetic field comprises:
analyzing, by the current closed loop magnetic field controller, a direction of the rotating magnetic field and a coil output current fed back by the current sensor to output the control signal to the PWM inverter circuit, and outputting, by the PWM inverter circuit, a desired current to the Helmholtz coil to generate the desired magnetic field, $$B = \begin{bmatrix} B_X \\ B_Y \\ B_Z \end{bmatrix} =$$

$$\frac{B_0\cos(2\pi ft)}{\sqrt{n_x^2+n_y^2}}\begin{bmatrix} n_y \\ -n_x \\ 0 \end{bmatrix} + \frac{B_0\sin(2\pi ft)}{\sqrt{(n_y n_z)^2 + (-n_y n_z)^2 + (-n_x^2 - n_y^2)^2}}\begin{bmatrix} n_y n_z \\ -n_y n_z \\ -n_x^2 - n_y^2 \end{bmatrix},$$

wherein $B_X$, $B_Y$, and $B_Z$ are components of a magnetic field B in three axial directions, and $n_x$, $n_y$ and $n_z$ are unit direction quantities of three planes, comprising an XOY plane, an XOZ plane, and a YOZ plane; and
decomposing a magnetic field into three axes, comprising an X axis, a Y axis, and a Z axis, a mapping relationship between a magnetic field and a current between the axes being as follows:

$$B = \left(\frac{4}{5}\right)^{\frac{3}{2}}\frac{\mu_0 NI}{a},$$

wherein $\mu_0$ is a magnetic field dielectric constant, N represents the number of turns of each Helmholtz coil, a represents a radius of the Helmholtz coil, and I represents the desired current flowing into the coil.

9. The micro-robot control method based on double closed loop three-dimensional path tracking according to claim 6, wherein in a case of no disturbance, a desired direction of movement of the magnetic micro-robot is an axial direction of the magnetic micro-robot, the desired direction of movement is represented by a first direction angle and a first pitch angle, the first direction angle is an angle between a projection of a vector $v_p$ to an XOY plane and an X axis, the first pitch angle is an angle between a vector $v_p$ and the XOY plane, due to the impact of gravity and disturbance, the actual axial direction of the magnetic micro-robot is represented by a second direction angle and a second pitch angle, and then a direction compensation is performed on the operating magnetic micro-robot to obtain a corresponding relationship between the actual axial direction and a desired direction of movement: $\theta_{d1}=\theta_d-\delta_{\theta d}$, and $\theta_{i1}=\theta_i-\delta_{\theta i}$, wherein $\theta_{d1}$ is the second direction angle, $\theta_d$ is the first direction angle, $\delta_{\theta d}$ is a compensation direction angle in a horizontal plane, the horizontal plane is the XOY plane, $\theta_{i1}$ is the second pitch angle, $\theta_i$ is the first pitch angle, $\delta_{\theta i}$ is a compensation pitch angle in a vertical plane, and the vertical plane is a plane perpendicular to the XOY plane;

the direction angle error is $\theta_{de}=\theta_{d1}-\theta_{dc}$, wherein $\theta_{dc}$ is a desired direction angle;

the pitch angle error is $\theta_{ie}=\theta_i-\delta_{\theta i}-\theta_{ic}$, wherein $\theta_{ic}$ is a desired pitch angle;

an actual movement speed of the operating magnetic micro-robot is:

$$v = \frac{1}{\cos\delta_{\theta i}\cos\delta_{\theta d}}v_p,$$

wherein $v_p$ is a desired movement speed, and v is an actual movement speed.

10. The micro-robot control method based on double closed loop three-dimensional path tracking according to claim 5, wherein the curve coordinate system of the desired tracking path is established with the desired position point as the origin, a tangential direction, a primary normal direction, and a secondary normal direction of the desired position point as coordinate axes, the tangential direction is the desired direction of movement, and a conversion relationship between the actual axial direction of the magnetic micro-robot and a first direction angle and a first pitch angle is obtained by the following formula:

$$X_B = \begin{bmatrix} \cos\theta_i \cos\theta_d \\ \cos\theta_i \sin\theta_d \\ \sin\theta_i \end{bmatrix}.$$

* * * * *